(12) United States Patent
Siderov

(10) Patent No.: US 6,221,918 B1
(45) Date of Patent: Apr. 24, 2001

(54) COMBINATION OF CAROTENOIDS FOR USE AS DIETARY SUPPLEMENT OR TOPICAL OINTMENT

(75) Inventor: Sergey V. Siderov, New York, NY (US)

(73) Assignee: Siberian Center for Natural Technologies, Inc., Staten Island, NY (US)

( * ) Notice: Subject to any disclaimer, the term of this patent is extended or adjusted under 35 U.S.C. 154(b) by 0 days.

(21) Appl. No.: 09/389,688

(22) Filed: Sep. 5, 1999

(51) Int. Cl.[7] .................................................. A01N 27/00

(52) U.S. Cl. ............................................................ 514/762

(58) Field of Search ................................ 424/195.1, 401, 424/404, 408, 410; 514/762

(56) References Cited

U.S. PATENT DOCUMENTS 5,858,761 * 1/1999 Tsubokura et al. ............... 435/252.1

FOREIGN PATENT DOCUMENTS

126108642 * 10/1995 (CA).
1156689 * 5/1985 (SU).

OTHER PUBLICATIONS

Hoffman, D. The Herbal Handbook; pp. 206–209, 1987.*

* cited by examiner

Primary Examiner—Jon P. Weber
Assistant Examiner—Patricia Patten

(57) ABSTRACT

A liquid health supplement comprising: (i) from about 1% to about 99% of a combination of at least 150 different carotenoid compounds with structures having chemical formula I:

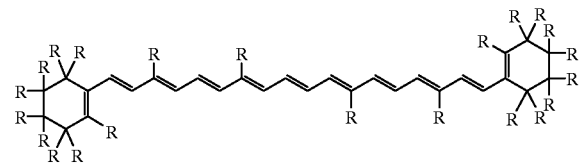

wherein each R group is the same or different and is selected from the group consisting of hydrogen, straight chain or branched $C_{1-8}$ alkyl, straight chain or branched $C_{1-8}$ alkenyl, straight chain or branched $C_{1-8}$ alkynyl, hydroxy, straight chain or branched $C_{1-8}$ alkoxy, keto, carboxyl, cyano, nitro amino, amide, ester, ether, halogen, substituted acyclic, substituted or unsubstituted cyclic, aromatic and heteroaromatic; and, (ii) an oil in an amount sufficient to mask the smell of the carotenoid compounds selected from the group of natural plant oils obtained from plant matter.

14 Claims, No Drawings

COMBINATION OF CAROTENOIDS FOR USE AS DIETARY SUPPLEMENT OR TOPICAL OINTMENT

FIELD OF THE INVENTION

The present invention relates to the use of oil based compositions containing combinations of more than 150 different carotenoid compounds as an orally administered health supplement or as a topical skin ointment wherein the composition is rendered non-odorous through use of a sunflower oil base.

BACKGROUND OF THE INVENTION

There is a continuing and growing demand in the United States for non-prescription medicaments which have a beneficial impact on the body and which do not require an office visit to a physician for use.

SUMMARY OF THE INVENTION

A liquid health supplement comprising: (i) from about 1% to about 99% of a combination of at least 150 different carotenoid compounds having structures of chemical formula I:

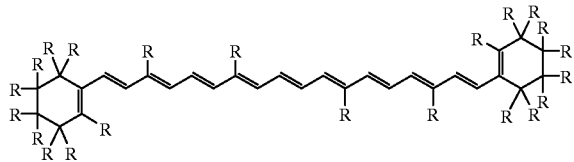

wherein each R group is the same or different and is selected from the group consisting of hydrogen, straight chain or branched C1–8 alkyl, straight chain or branched C1–8 alkenyl, straight chain or branched C1–8 alkynyl, hydroxy, straight chain or branched C1–8 alkoxy, keto, carboxyl, cyano, nitro amino, amide, ester, ether, halogen, substituted acyclic, substituted or unsubstituted cyclic, aromatic and heteroaromatic; and, (ii) a oil in an amount sufficient to mask the smell of the carotenoid compounds selected from the group of natural plant oils obtained from plant matter.

DETAILED DESCRIPTION OF THE INVENTION

The present invention is directed to a liquid health supplement comprising: (i) from about 1% to about 99% of a combination of at least 150 different carotenoid compounds with structures having chemical formula (I):

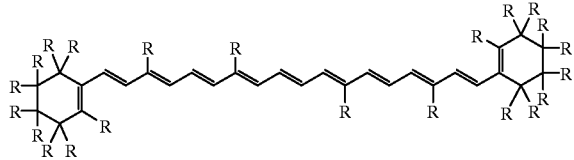

wherein each R group is the same or different and is selected from the group consisting of hydrogen, straight chain or branched $C_{1-8}$ alkyl, straight chain or branched $C_{1-8}$ alkenyl, straight chain or branched $C_{1-8}$ alkynyl, hydroxy, straight chain or branched $C_{1-8}$ alkoxy, keto, carboxyl, cyano, nitro amino, amide, ester, ether, halogen, substituted acyclic, substituted or unsubstituted cyclic, aromatic and heteroaromatic; and, (ii) a oil in an amount sufficient to mask the smell of the carotenoid compounds selected from the group of natural plant oils obtained from plant matter.

For purposes of this invention the R groups attached to the caratene backbone may be the same or different. The skilled artisan will be able to appreciate that the R groups may be all hydrogen, all methyl or a combination of some hydrogen and some methyl. Another example would be a compound where the R groups are each different. Thus the scope of the present invention is intended to include at least 150 different carotenoid compounds falling within the broad genus of all carotenoid compounds.

It will be appreciated by those skilled in the art that the numbering of the backbone system for individual compounds within the scope of formula (1) will vary according to the nature, number and position of substituents.

It will also be appreciated that the compounds of formula (1) may contain a chiral centre. It is to be understood that formula (1) is intended to encompass all enantiomers and diasteroisomers of the compounds of the invention as well as mixtures thereof, including racemates.

The definition of the substituent group R is broad and includes any structural moiety selected from the group comprising cyano, nitro, halogen, oxygen, hydroxy, straight or branched chain alkoxy, thio, straight or branched chain alkyl, carbocyclic aryl and substituted or heterocyclic derivates thereof, wherein R may be the same or different in all possible combinations and permutations.

As used herein, the phrase straight or branched chained alkyl groups means any substituted or un-substituted acyclic carbon-containing compounds, including alkanes, alkenes and alkynes. Alkyl groups having up to 30 carbon atoms are preferred. Examples of alkyl groups lower alkyl, for example, methyl, ethyl, n-propyl, iso-propyl, n-butyl, iso-butyl or tert-butyl; upper alkyl, for example, octyl, nonyl, decyl, and the like; lower alkylene, for example, ethylene, propylene, propyldiene, butylrene, butyldiene; upper alkenyl such as 1-decene, 1-nonene, 2.6-dimethyl-5-octenyl, 6-ethyl-5-octenyl or heptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, for example, alkoxy polyhydroxy such as 1.2-dihydroxypropyl, 1.4-dihydroxy-1-butyl, and the like; methylamino, ethylamino, dimethylamino, diethylamino, triethylamino, cyclopentylamino, benzylamino, dibenzylamino, and thre like; propanoic, butanamido, and the like, methoxycarbonyl, ethoxycarbonyl or the like, chloroformyl, bromoformyl, 1,1-chloroethyl, bromoethyl, and the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. Such cyclic groups may also contain various substituents in which one or more hydrogen atoms has been replaced by a functional group. Such functional groups include those described above, and lower alkyl groups as described above. The cyclic groups of the invention may further comprise a heteroatom.

As used herein, substituted ad unsubstituted aryl groups means a hydrocarbon ring bearing a system of conjugated double bonds, usually comprising an even number of 6 or more (pi) electrons. Examples of aryl groups include, but are not limited to, phenyl, naphthyl, anisyl, toluyl, xylenyl and the like. According to the present invention aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocylic groups, functional groups on the aryl groups can be nitro groups.

As mentioned above, these structural moieties can also be any combination of alkyl, carbocyclic or aryl groups, for example, 1-cyclohexylpropyl, benzylcyclohexylmethyl, 2-cyclohexyl-propyl, 2,2-methylcyclohexylpropyl, 2,2 methylphenylpropl, 2,2-methyphenylbutyl, and the like.

The mixture of at least 150 different carotenoid compounds may be obtained from a variety of sources. For example it is currently possible to synthesize large numbers of carotenoid compounds using bacteria. This method is described for example in U.S. Pat. No. 5,858,761, issued Jan. 12, 1999, to Tsubokura et al. This methodology can be used to involves the separate production of at least 150 different carotenoids and the subsequent mixture of these compounds. The advantage of this method is that the individual carotenoid compounds may be individually chosen and then added in their most beneficial proportions. The disadvantages of this method is that it is expensive.

Another method is to obtain the carotenoid compounds from natural sources such as plants and aquatic life. Carotenoid compounds come from a variety of different plant life in varying concentrations and varieties. For example the yellow and orange vegetables such as carrots, different squashs and pumpkins, for example contain a variety of different carotenoid compounds which can be used according to the present invention. Although these sources do not typically yield the at least 150 carotenoid compound variety of the present invention, the extracts of more than one of these plants can be combined to yield the desired variety necessary for the present invention.

Another option is to use extract from plant life that contains the variety of carotenoids is to employ the extracts of plants which contain large varieties and great concentrations of carotenoids necessary for the present invention. Some varieties of the sea buck thorn plant, also known as *Hippophae rhamnoides*, can produce the large variety of carotenoids desirable for use in the present invention. For example, some new varieties of sea buckthorn plant can yield carotenoid mixtures containing over 180 different varieties of carotenoids.

The number of different varieties of carotenoid compounds making up the mixture can vary from about 150 up to about 400. The lower levels of carotenoid varity have been associated with relatively weaker healing properties than for example a mixture containing 180 or more different carotenoid compounds. Accordingly, it is preferable to use a higher number of different carotenoid compounds in the mixture according to the present invention.

One draw back with the use of carotenoids is the unpleasant odor associated with their use. The odor can be so unpleasant as to dissuade many consumers from using a beneficial product containing carotenoids. Surprisingly, it has been found that substantially pure sunflower seed oil masks the smell typically associated with carotenoids, and Sea buckthorn extract in particular, that many consumers otherwise unwilling, will imbibe a composition comprising the carotenoid mixture and sunflower seed oil. Accordingly, one of ordinary skill in the art will appreciate the advantages of the sunflower seed oil and Sea buckthorn combination. Other plant oils may also be used as a base for the carotenoid combination however. Vegetable oils such as safflower oil, corn oil, peanut oil, sesame oil, cannola oil, soy oil, soybean oil, burdock root oil and olive oil can also be employed albeit with varying and less successful degrees of odor control and therefore consumer palatability. Other oil bases, such as shark liver oil, cod liver oil and fish liver oil may also be used.

The preferred oil used as a base for the health supplement is substantially pure. For purposes of the present invention, the term "substantially pure" means containing less than 0.50 % impurites.

The ratio of carotenoid mixture to oil base can vary widely and can be any ratio sufficient to deliver a desired dose of carotenoid compounds. The skilled artisan that the amount of carotenoid will vary depending on the therapeutic goals of the composition. For example, the carotenoid mixture can vary from 0.01% to about 50.00% of total volume with adequate odor suppression for general consumer acceptability. Another range found more adequate to deliver a therapeutic dosage of the carotenoid mixture is from about 1% to about 25% of the carotenoid mixture. The range of carotenoid mixture that is currently viewed as an optimal balance between carotenoid dosage while limiting odor is from about 5% to about 25% carotenoid mixture to total composition volume.

Similarly, the amount of oil base can vary widely depending on the therapeutic goals of the composition. Since the amount and kind of oil base will have an impact on odor and dosage properties of the health supplement, it will be appreciated that the amount of oil base can vary depending on the desired properties of the final composition. The amount of oil can vary from about 50.00% to about 99.99% of the total volume of the composition. The preferred volume of oil base is from 75.00% to about 99.00% of the total compositional volume. The optimum oil volume ranges from 75% to about 95% when the oil base used is sunflower oil.

The present invention also contemplates the use of any vitamin in combination with the present combination of an oil base and a carotenoid mixture. Vitamins such as A, $B_1$, $B_2$, $B_6$, $B_{12}$, C, D and E can be added in any amount to improve the therapeutic effect of the present invention.

Other common additives may be added to the carotenoid mixture and the oil base composition of the present invention to improve processing, long term potency or consumer acceptance of the present health additive. Common additives such as binders, excipients, flow regulating agents, thinners, perfuming agents and ultra violet light absorbers may be used in those amounts as can be easily determined using common test procedures to improve the properties of the present health supplement.

In addition to its liquid form, the present invention is also contemplated for use as a lotion. The carotenoid mixture of the present invention has been found to have a material and beneficial impact on the time it takes for mild bums and otherwise inflamed skin to heal.

It is preferred to dispense the instant health supplement in containers that prevent the decomposition of carotenoid efficacy through exposure to sunlight. This may be accomplished in any way known in the art. The preferred method is to package the liquid composition in dark bottles which reduce the amount UV radiation affecting the stored liquid.

The health supplements according to the present invention can be made in a variety of ways well known to the skilled artisan. One simple way is to measure appropriate amounts of the carotenoid mixture and oil base and then mix together. Other similarly simple methods of preparing the liquid dosage preparation will be apparent to the person of ordinary skill in the art.

When making capsules or gel caps, it is preferred to use the liquid health supplement comprising the carotenoid mixture and oil base as the filling. Methods of making capsules and gel caps are well known in the art. Indeed any known method of making pharmaceutical dosage forms, such as those described in Remington Pharmaceutical Sciences, 16th Edition, Mack Publishing Company, Easton, Pa., 1980, may be employed in the manufacture of health supplements according to the present invention.

All aforementioned patents, patent applications and other publications are herein incorporated by reference in their entirety as though set forth in full.

The following examples illustrate the subject invention and should not be construed as limiting the scope of the claimed invention. All amounts are in parts by weight of the total composition unless otherwise specified.

EXAMPLES

Example 1

10 grams each of 151 different carotenoids are combined in a mixing bowl and thoroughly mixed for 10 minutes. After the mixture is uniform 2 liters of substantially pure sunflower oil is added to the mixing bowl and stirred until the composition has a light burnt orange color. The composition is then metered into bottles having a 100 ml capacity.

Example 2

Berries from Sea buckthorn plants are pressed until all free running fluid is removed from the plant matter with the pressed fluid collected in a large bowl. A 25/75 blend of pure ethyl alcohol and water is added to the Sea buckthorn fluid so collected and allowed to sit overnight. The next morning the alcohol is removed from the bowl through evaporation under a vacuum. The resultant mixture containing carotenoids is further reduced to a concentrate through evaporation to 5% of the original volume ethyl alcohol and water added. The resulting concentrate of carotenoids is saved for future use.

Example 3

250 ml of concentrate from example 2 is mixed with 50 ml of Vitamin E and 0.75 liters of cod liver oil. The resulting combination is blended to a uniform consistency and color and then metered in 100 ml bottles for individual sale.

Example 4

The following ingredients are thoroughly mixed to a milky consistency:

| | |
|---|---|
| Carotenoid concentrate from example 2 | 10.00 |
| Tetraoctylqueraetin | 0.20 |
| Abil WE 09 | 5.00 |
| paraffin oil, highly liquid (Art. No. 7174) | 35.00 |
| Paraffin wax | 3.00 |
| Demineralized water | qs 100.00 |

Example 5

The following ingredients are thoroughly mixed to a milky consistency:

| | |
|---|---|
| Carotenoid concentrate from example 2 | 10.00 |
| Sweet almond oil | 4.00 |
| Grapeseed oil | 8.00 |
| Sunflower oil | 8.00 |
| Volatile silicone oil | 3.00 |
| Fragrance | 0.20 |
| Polycarboxyvinylic acid mixture marketed under the name "Carbopol". (gelling agent) by the company Goodrich | 0.42 |
| Triethanolamine | qs pH = 6 |
| Demineralized water | qs 100.00 |

Example 6

The following ingredients are thoroughly mixed to a milky consistency:

| | |
|---|---|
| Carotenoid concentrate from example 2 | 10.00 |
| Butylene glycol | 20.00 |
| Propylene glycol | 15.00 |
| Citric acid | 00.02 |
| Sodium Citrate | 00.05 |
| Melatonin | 02.00 |
| Fragrance | 00.05 |
| Preservative | 00.10 |
| Demineralized water | qs 100.00 |

Example 7

The following ingredients are thoroughly mixed to a uniform consistency to form an aqueous Gel:

| | |
|---|---|
| Carotenoid concentrate from example 2 | 10.00 |
| Isoprene glycol | 20.00 |
| Glycerol | 05.00 |
| Acrylate/C10–C30 alkyl acrylate crosslinked copolymer (Pemulen TR2, marketed by Goodrich) | 00.50 |
| Phenylethyl alcohol | 00.50 |
| Melatonin | 00.50 |
| Diazolidinylurea | 00.10 |
| Demineralized water | qs 100.00 |

Example 8

The following ingredients are thoroughly mixed to a uniform consistency to form an aqueous face lotion:

| | % by weight |
|---|---|
| Carotenoid concentrate from example 2 | 08.000 |
| PEG 40-hydrogenated castor oil | 00.811 |
| Dipropylene glycol | 02.534 |
| PEG 8 | 01.521 |
| Na3EDTA | 00.253 |
| Polymer JR 125 | 00.025 |

-continued

|  | % by weight |
|---|---|
| UCA | 00.750 |
| Demineralized water | qs 100.00 |

Example 9

The following ingredients are thoroughly mixed to a milky consistency:

|  | % by weight |
|---|---|
| Carotenoid concentrate from example 2 | 10.00 |
| Poly-fatty acid ester (Cetiol HE) | 16.00 |
| PPG 3-myristyl ether (Witconol APM) | 1.00 |
| Propylene glycol | 3.00 |
| Glycerol | 40.00 |
| UCA | 0.50 |
| Demineralized water | qs 100.00 |

Example 10

The following ingredients are thoroughly mixed to a uniform consistency to form a Hydrogel (Polyacrylate Gel):

|  | % by weight |
|---|---|
| Carotenoid concentrate from example 2 | 10.00 |
| Acrylic acid polymer (Carbopol 934) | 1.00 |
| Tris (hydroxymethylamino) methane (Tris) | 1.00 |
| Glycerol | 2.00 |
| Propylene glycol | 2.00 |
| UCA | 0.05 |
| Demineralized water | qs 100.00 |

Example 11

The following ingredients are thoroughly mixed to a uniform blend to form a high water content semi-solid:

|  | % by weight |
|---|---|
| Carotenoid concentrate from example 2 | 10.000 |
| Ceteareth-25 | 3.000 |
| Cetearyl alcohol (Lanette O) | 17.000 |
| UCA | 0.175 |
| Demineralized water | qs 100.00 |

Example 12

The following ingredients are thoroughly mixed to a milky consistency to make a thinly mobile lotion

|  | % by weight |
|---|---|
| Carotenoid concentrate from example 2 | 10.000 |
| Ceteareth-25 (Cremophor A25) | 1.000 |
| Ceteareth 6-stearyl alcohol | 1.000 |

-continued

|  | % by weight |
|---|---|
| (Cremophor A6) |  |
| Glycerol mono-distearate (Tegin normal) | 2.000 |
| Cetyl alcohol | 1.000 |
| Isopropyl myristate | 1.450 |
| Glycerol | 1.000 |
| Polyvinyl pyrrolidone | 0.500 |
| UCA | 0.129 |
| Demineralized water | qs 100.00 |

Example 13

The following ingredients are thoroughly mixed to a uniform consistency to form a Viscous Lotion:

|  | % by weight |
|---|---|
| Carotenoid concentrate from example 2 | 10.00 |
| Ceteareth 25 (Cremophor A25) | 2.00 |
| Cetearyl alcohol (Lanette O) | 3.00 |
| Mineral Oil, GP9 | 5.00 |
| Propylene glycol | 3.00 |
| Polyvinylpyrrolidone | 0.50 |
| UCA | 0.30 |
| Demineralized water | qs 100.00 |

Example 14

The following ingredients are thoroughly mixed to a creamy and uniform consistency:

|  | % by weight |
|---|---|
| Carotenoid concentrate from example 2 | 10.00 |
| Glycerol sorbitan fatty acid ester (Arlacel 481) | 6.00 |
| Microcrystalline wax (lunacera M) | 1.00 |
| Neutral oil | 3.00 |
| Paraffin oil | 19.00 |
| Magnesium stearate | 1.00 |
| Propylene glycol | 3.70 |
| Magnesium sulphate (MgSO4.7 H2O) | 0.70 |
| UCA | 1.00 |
| Demineralized water | qs 100.00 |

Example 15

The following ingredients are thoroughly mixed to a milky consistency:

|  | % by weight |
|---|---|
| Carotenoid concentrate from example 2 | 10.00 |
| Polyoxyethylene glycerol sorbitan fatty acid ester (Arlacel 988) | 3.60 |
| Polyoxyethylene fatty acid ester (Arlacel 989) | 1.40 |
| Cetearyl alcohol (Lanette O) | 2.00 |
| Mineral oil, GP 9 | 25.00 |
| Paraben mixture | as required |

-continued

|  | % by weight |
|---|---|
| Magnesium sulphate (MgSO4.7 H2O) | 0.70 |
| UCA | 1.25 |
| Water DEM | qs 100.00 |

Example 16

The following ingredients are thoroughly mixed to a milky consistency to form a lotion:

|  | % by weight |
|---|---|
| Glycerol sorbitan fatty acid ester (Arlacel 481) | 1.30 |
| Polyoxyethylene fatty acid ester (Arlacel 989) | 3.70 |
| Neutral oil (Miglyol) | 6.00 |
| Paraffin oil, GP 9 | 14.00 |
| Propylene glycol | 3.80 |
| Magnesium sulfphate (MgSO4.7 H2O) | 0.70 |
| UCA | 0.06 |
| Water DEM | qs 100.00 |

Example 17

The following ingredients are thoroughly mixed to a milky consistency:

|  | % by weight |
|---|---|
| Carotenoid concentrate from example 2 | 10.000 |
| PEG 100 stearate (Arlacel 165) | 5.000 |
| Cetearyl alcohol (Lanette O) | 3.000 |
| Mineral oil, GP 9 | 25.000 |
| Paraben Mixture | as required |
| UCA | 0.325 |
| Demineralized water | qs 100.00 |

Example 18

The following ingredients are thoroughly mixed to a uniform consistency:

|  | % by weight |
|---|---|
| Carotenoid concentrate from example 2 | 10.000 |
| Polysorbate 60 (Tween 60) | 3.000 |
| Saorbitan stearate (Arlacel 60) | 2.000 |
| Cetearyl alcohol (Lanette O) | 3.000 |
| Mineral oil, P9 | 25.000 |
| Paraben mixture | as required |
| UCA | 0.035 |
| Demineralized water | qs 100.00 |

Example 19

The following ingredients are thoroughly mixed to a uniform consistency:

|  | % by weight |
|---|---|
| Carotenoid concentrate from example 2 | 10.00 |
| Distearyldimethylammonium chloride (Genamin DS Ac) | 5.00 |
| Vaseline, GP9 | 5.00 |
| Isopropyl palmitate | 2.00 |
| Cetyl alcohol | 1.00 |
| Silicone oil | 0.10 |
| Propylparaben | 0.10 |
| Methylparaben | 0.10 |
| Glycerol | 4.00 |
| UCA | 0.09 |
| Demineralized water | qs 100.00 |

Example 20

The following ingredients are thoroughly mixed to a uniform consistency:

|  | % by weight |
|---|---|
| Carotenoid concentrate from example 2 | 10.00 |
| Sodium cetearyl sulphate (Emulgade F) | 6.00 |
| Mineral oil, GP9 | 25.00 |
| Paraben mixture | as required |
| UCA | 0.45 |
| Water DEM | qs 100.00 |

Example 21

The following ingredients are thoroughly mixed to a uniform consistency:

|  | % by weight |
|---|---|
| Carotenoid concentrate from example 2 | 10.00 |
| Stearic acid | 5.00 |
| Cetearyl alcohol (Lanette O) | 3.00 |
| Mineral oil, GP 9 | 25.00 |
| Paraben mixture | as required |
| Triethanolmine | 12.00 |
| UCA | 0.08 |
| Mineralized water | qs 100.00 |

Example 22

Ten patients suffering from mild burns are either treated by applying lotion made according to example 7 to the burn area or left untreated. After eight days the patients are evaluated to determine whether the skin tissue has healed and to what extent. A plus sign indicates that the burn is healed or that there is scarring. A minus sign indicates that the burn has not healed or that there is no scarring. An n/a indicates that it is still too early to see if scarr tissue will be noticeable.

|  | Amount healed | Scarring |
| --- | --- | --- |
| Treated Patient #1 | + | − |
| Treated Patient #2 | + | − |
| Treated Patient #3 | − | n/a |
| Treated Patient #4 | + | − |
| Treated Patient #5 | + | − |
| Untreated Patient #6 | − | n/a |
| Untreated Patient #7 | − | n/a |
| Untreated Patient #8 | − | n/a |
| Untreated Patient #9 | + | + |
| Untreated Patient #10 | + | + |

Based on the above, it was concluded that a mixture of carotenoids according to the present invention is useful in the treatment of burns to promote fast healing and reducing scarring.

The skilled artisan will appreciate that the health supplement disclosed can be made and used in a variety of ways without departing from the scope of the invention embodied in the following claims

I claim:

1. A liquid health supplement consisting essentially of:
   (i) from about 1% to about 99% of a combination of at least 150 different carotenoid compounds with structures having chemical formula I:

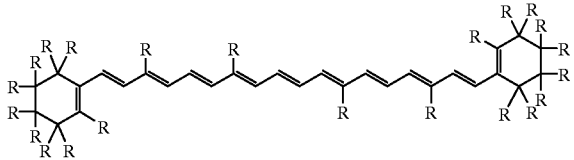

wherein each R group is the same or different and is selected from the group consisting of hydrogen, straight chain or branched $C_{1-8}$ alkyl, straight chain or branched $C_{1-8}$ alkenyl, straight chain or branched $C_{1-8}$ alkynyl, hydroxy, straight chain or branched $C_{1-8}$ alkoxy, keto, carboxyl, cyano, nitro amino, amide, ester, ether, halogen, substituted acyclic, substituted or un-substituted cyclic, aromatic and heteroaromatic; and,
   (ii) an oil base in an amount sufficient to mask the smell of the carotenoid compounds selected from the group of natural oils.

2. A liquid health supplement according to claim 1 wherein the supplement comprises a combination of at least 160 different carotenoid compounds.

3. A liquid health supplement according to claim 1 wherein the supplement comprises a combination of at least 170 different carotenoid compounds.

4. A liquid health supplement according to claim 1 wherein the supplement comprises a combination of at least 180 different carotenoid compounds.

5. A liquid health supplement according to claim 1 wherein the oil base used is a vegetable oil selected from the group consisting of corn oil, sunflower oil, cannola oil, grape seed oil, olive oil, safflower oil and peanut oil.

6. A liquid health supplement according to claim 5 wherein the oil base is sunflower oil.

7. A liquid health supplement according to claim 1 wherein the oil base is selected from the group consisting of cod liver oil, shark liver oil and fish liver oil.

8. A liquid health supplement according to claim 1 wherein the carotenoid component consists essentially of from between 1% to about 50.00% of the total volume of the supplement and the oil component comprises from about 50.00% to about 99% of the total volume of the supplement.

9. A liquid health supplement according to claim 1 wherein the carotenoid component consists essentially of from between 1.00% to about 25.00% of the total volume of the supplement and the oil component comprises from about 75.00% to about 99.00% of the total volume of the supplement.

10. A liquid health supplement according to claim 1 wherein the carotenoid component consists essentially of from between 5.00% to about 25.00% of the total volume of the supplement and the oil component comprises from about 75.00% to about 95.00% of the total volume of the supplement.

11. A liquid health supplement according to claim 1 wherein individual carotenoid compounds are combined to provide a combination of 150 or more carotenoid compounds.

12. A liquid heath supplement according to claim 1 encapsulated as a gel cap or capsule for oral administration.

13. A method of supplementing the diet of a patient comprising orally administering the gel cap or capsule according to claim 12.

14. A method of treating an area of skin inflammation comprising topically administering the composition of claim 1 to a patient in need thereof.

* * * * *